United States Patent [19]

Boyer

[11] 4,085,748
[45] Apr. 25, 1978

[54] SYRINGE INJECTOR

[76] Inventor: Emanual F. Boyer, 4826 Oak Orchard Rd., Albion, N.Y. 14411

[21] Appl. No.: 737,275

[22] Filed: Nov. 1, 1976

[51] Int. Cl.² .............................................. A61M 5/00
[52] U.S. Cl. ................................. 128/215; 128/218 F
[58] Field of Search ................... 128/215, 216, 218 R, 128/218 F, 218 A, 234

[56] References Cited

U.S. PATENT DOCUMENTS

| 3,605,743 | 9/1971 | Arce | 128/218 F |
| 3,612,051 | 10/1971 | Arce | 128/215 |
| 3,702,608 | 11/1972 | Tibbs | 128/218 F |

FOREIGN PATENT DOCUMENTS 394,498  11/1965  Switzerland .......................... 128/215

Primary Examiner—John D. Yasko

[57] ABSTRACT

The device comprises a base plate and a cover plate held in spaced, parallel relation by a pair of spaced, parallel side walls. A rectangular rib, which extends between the sidewalls approximately midway between the base and cover plates, has therein a central, circular opening which registers coaxially with like openings in the base and cover plates. A cocking bar, which is reciprocable between the side walls beneath the rib, has a central opening movable into and out of registry with the opening in the rib. In use, the cocking bar is shifted to offset its opening slightly from the opening in the rib; and a syringe is inserted, needle-down, through the openings in the cover plate, rib and cocking bar, but with the lower end of the syringe barrel or housing seated on a marginal portion of the cocking bar around its now-offset opening. A resilient member is placed over a shoulder on the upper end of the syringe housing, so that when the opening in the base plate is positioned over the spot into which the needle is to be inserted, the operator needs only to shift the cocking bar slightly to register its opening with that in the rib. The lower end of the syringe thus slides off the retaining portion of the cocking bar and is urged suddenly down to project its needle through the opening in the base plate and into the operator's body.

6 Claims, 3 Drawing Figures

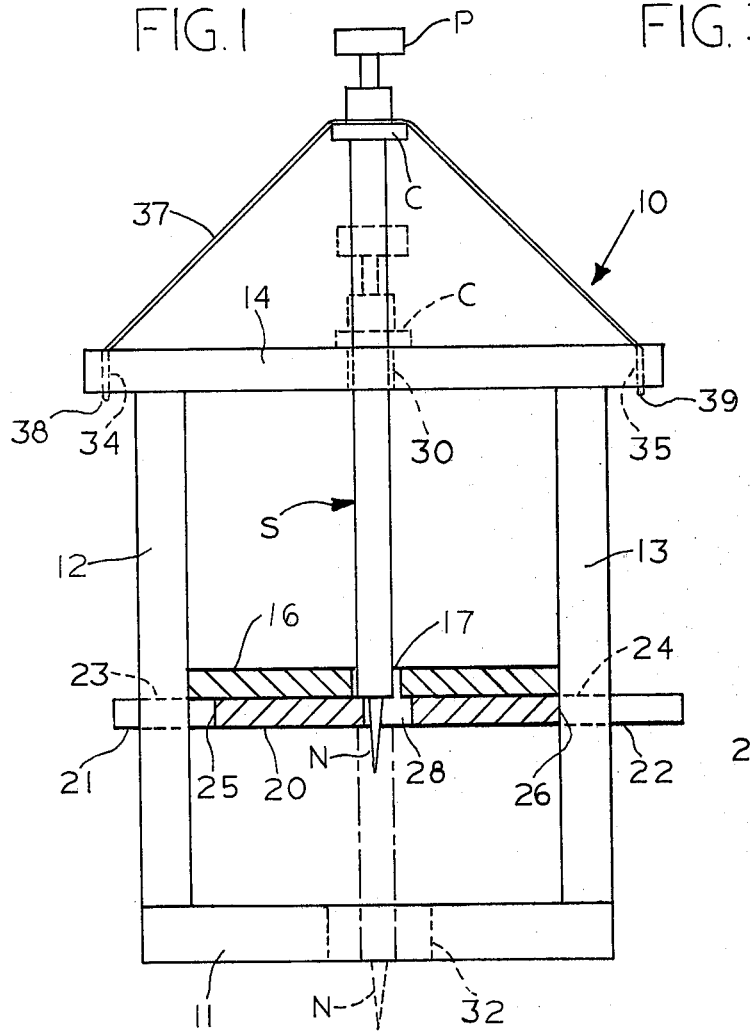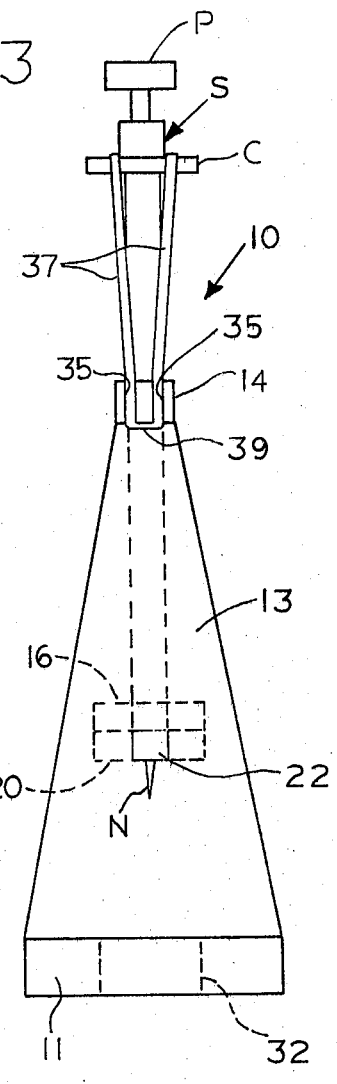

SYRINGE INJECTOR

This invention relates to syringes, and more particularly to a novel device for mechanically inserting the needle of a syringe into a person's body in advance of injecting the contents of the syringe into the body.

It is not uncommon for individuals, particularly those afflicted with sugar diabetes, to administer to themselves their own medicine. Frequently this is done through the use of syringes, as for example in the case of administration of insulin a diabetic.

A major difficulty experienced by many such individuals, however, is the necessity of having to insert the needle of a syringe into one's own body in order to be able to inject its contents properly into an arm, leg or the like. Since many illnesses require the injection of a medicine or drug several times a day, the very act of having to insert the needle, once again, into one's body can be a rather traumatic experience.

It is an object of this invention, therefore, to provide for individuals of the type described a novel device which can be utilized nearly automatically to insert or inject the needle of a syringe into one's body rapidly and accurately, and with minimum pain.

A further object of this invention is to provide a device of the type described which is inexpensive to manufacture, and extremely simple to operate.

Other objects of the invention will be apparent hereinafter from the specification and from the recital of the appended claims, particularly when read in conjunction with the accompanying drawing.

In the drawing:

FIG. 1 is a front elevational view of a syringe injecting device made according to one embodiment of this invention, portions of the device being broken away and shown in section for purposes of illustration;

FIG. 2 is a plan view of this device;

FIG. 3 is a side elevational view of this device.

Referring now to the drawing by numerals of reference, 10 denotes generally a syringe injector comprising a plane, rectangular base 11, a pair of spaced, registering, parallel side walls 12 and 13, and an elongate, rectangular cover plate 14. The side walls 12 and 13, which are generally truncated-triangular in configuration, have their lower, wider ends secured to the upper surface of base 11 adjacent opposite ends thereof, and their upper, narrow ends secured to the underside of plate 14 adjacent to, but slightly inwardly of its ends.

Secured at opposite ends to the inside surfaces of the side walls 12 and 13, and extending transversely between these walls in spaced, parallel relation to the base 11 and cover plate 14, is a rectangular plate or rib 16, which has therethrough a central, circular opening 17. Plate 16 is located slightly below the midpoint of the distance separating the base 11 and the cover plate 14.

Mounted immediately beneath plate 16 with its plane upper surface disposed in sliding, coplanar contact with the underside of the rib 16 is a reciprocable latching plate 20. Integral with, and projecting from opposite ends, respectively, of plate 20 are two rectangular projections 21 and 22, which are slidable in registering, rectangular apertures 23 and 24 formed in the side walls 12 and 13, respectively. The projections 21 and 22 may be formed on the plate 20 by notching or otherwise removing rectangular portions of plate 20 at each end thereof, and along opposite sides thereof, so that transverse shoulders 25 and 26 are formed adjacent opposite ends of plate 20 at its junctures with projections 21 and 22, respectively.

The shoulders 25 and 26 on plate 20 are spaced from each other a distance less than the space separating the side walls 12 and 13, so that plate 20 can be reciprocated between the side walls by manipulating one or the other of its projections 21 and 22, both of which project beyond the outer surfaces of walls 12 and 13. For example, as illustrated in FIG. 1, the shoulder 26 on plate 20 is engaged against the inner surface of the side wall 13, at which time the other shoulder 25 on plate 20 is laterally spaced from the inside surface of wall 12. When the plate 20 is in this position, a circular aperture 28, which is located in the center of plate 20, and which has the same diameter as the aperture 17 in the plate 16, is slightly offset laterally or horizontally relative to the opening 17. On the other hand, when the plate 20 is shifted to its left hand position (not illustrated), for example by pushing on the outer end of the projection 22 until shoulder 25 engages the inner surface of wall 12, the aperture 28 will then be vertically aligned with the aperture 17 for a purpose noted hereinafter.

The cover plate 14 has through its center a circular aperture 30, which registers vertically with the aperture 17 in plate 16, and which has a diameter similar to those of apertures 17 and 28. The base plate 11 also has in its center a circular aperture 32, which is disposed coaxially of the apertures 17, 28 and 30, but which has a diameter slightly larger than the other apertures.

In each of its ends the cover plate 14 has a pair of spaced, parallel, notches 34 and 35 respectively. An elastic loop or rubber band 37 has diametrically opposite sides thereof hooked as at 38 and 39 beneath the portions of the cover plate 14 defined by the spaced notches 34 and 35.

In use, the plate 20 is manipulated into its cocked or right hand position as illustrated in FIG. 1, as for example by pushing on the outer end of projection 21, so that the aperture 28 in plate 20 is slightly offset laterally relative to the aperture 17 and plate 16. A conventional syringe, which is denoted generally at S in the drawing, is then placed in the injector 10 so that its needle N projects downwardly, as in FIG. 1, through the opening 28 in plate 20, and so that the lower end of its tubular, medicine-containing barrel is seated on a marginal portion of the upper surface of the plate 20 at the left hand (FIG. 1) side of the opening 28. At this time the upper end of the barrel of the syringe S extends slidably and upwardly through the opening 30 on the cover plate 14, and opposite sides of the band 37 are placed over opposite ends of the integral collar C, which projects from diametrically opposite sides of the syringe barrel in a conventional manner.

In this position the band 37 is tensioned, and the portions thereof which pass over the collar C urge the entire syringe S downwardly into its cocked position. At this point the syringe is prevented from being urged through the opening 28 in the plate 20 because of the engagement of the lower end of its barrel portion with the upper surface of the now-cocked plate 20.

It is to be understood that the needle N, and the sizes of the opening 17 and 28 are enlarged for purposes of illustration, and do not necessarily represent the exact dimensions of these elements. It is important, however, that the diameter of the opening 17 be large enough to permit the barrel of the syringe to slide vertically therein, as noted hereinafter, but at the same time it should not be so large that it will enable the barrel to slip or tilt out of the vertical far enough to permit its lower end accidentally to slide off of the upper surface of the plate 20 and downwardly through the opening 28 in plate 20.

After the syringe S has been placed in its cocked position as shown in solid lines in the drawing, the person using the injector 10 places the plane underside of the base 11 against his or her body so that the aperture 32 in plate 11 registers with that portion of the flesh or skin into which the needle N is to be inserted. After this has been done the person pushes on the outer end of the projection 22 to shift the plate 20 into its released position where shoulder 25 engages wall 12, so that the aperture 28 is shifted into alignment with the opening 17 in the plate 16. As soon as this occurs the resilient band 37 urges the entire syringe S suddenly downwardly from its upper to its lower or fired position as shown by broken lines in FIG. 1, wherein the collar C on the syringe seats against the upper surface of the cover plate 14. At this time needle N extends downwardly beneath the bottom of the base plate 11 and into that part of the body into which the contents of the syringe is to be injected. Then the operator manipulates the plunger P of the syringe in known manner to inject its contents into the person's body. Thereafter the entire device is withdrawn, thereby causing the needle N to be withdrawn from the person's body, after which the syringe, assuming that it is of the disposable variety, is withdrawn from the device 10 and discarded.

When it next becomes necessary to use the device 10, the cocking plate 20 is once again shifted back to its cocked position as illustrated in FIG. 1, so that when the next syringe S is placed in the device with its collar C located beneath the band 37, the lower end of this next syringe also will engage the upper surface of the plate 20 around a marginal portion of its opening 28 to retain the new syringe in its cocked position. The above procedure is then repeated in order to inject the needle of the new syringe into the person's body, when necessary.

From the foregoing it will be apparent that applicant has devised an extremely simple and inexpensive device for inserting syringe needles into the body of an individual. The device operates to inject the needle of the syringe so rapidly that there is little pain involved at the time that the needle penetrates the body. Furthermore, the tension applied by the band 37 to the syringe can be readily adjusted merely by changing the type of rubber band which is employed to inject the needle upon movement of the plate 20 to its fired position. Moreover, since the collar C is a standard portion of all conventional syringes S, the depth of the penetration of the needle N of any particular syringe S can be controlled merely by controlling the distance between the upper surface of plate 14 and the lower surface of plate 11. If desired, therefore, several different devices 10 can be utilized for each of which the distance between the upper and lower surfaces of the plates 14 and 11, respectively, will be different, depending upon the make of the syringe S employed. Obviously, also, the diameters of the openings 30, 17 and 28 can also be modified, as need be, depending upon the size of the syringe S employed.

Still another advantage of applicant's device is that the opening formed between the spaced plates 12 and 13 enables the operator to view the lower end of the syringe S, after the needle has been inserted into the body, so that if it is necessary for the operator to retract the plunger of the syringe slightly to determine whether or not a vein or artery has been encountered, the presence or absence of blood in the lower end of the barrel of the syringe can be readily determined by observation. Moreover, if desired, the components employed in manufacturing this device, for example the plates 11 to 14, 16 and 20, could be manufactured from rigid transparent material such as Plexiglas, or the like.

While the invention has been described in detail in connection with only a single embodiment thereof, it is nevertheless apparent that it is capable of further modification, and that this application and the appended claims are intended to cover any such modifications as may fall within the scope of one skilled in the art.

Having thus described my invention, what I claim is:

1. A device for inserting the needle of a syringe into a body, comprising a first pair of spaced members having therein a pair of registering openings, two additional members mounted adjacent each other in the space between said first pair of members, one of said additional members having therein an opening registering with the pair of openings in said first pair of members, means mounting the other of said additional members for movement selectively between a cocked position in which an opening herein is laterally offset slightly from the opening in said one additional member, and a fired position in which the opening therein registers with the opening in said one additional member, and resilient means mounted on one of said first pair of members and operable, when the other of said additional members is in its cocked position, releasably to support a syringe needledown in the opening in said one of said first pair of members with the lower end of said syringe urged resiliently against a marginal portion of said other additional member adjacent said opening therein, said marginal portion of said other additional member being movable from beneath said lower end of the syringe upon movement of said other additional member to its fired position, whereupon the syringe is urged suddenly downwardly through the now-registering openings in said members to inject the needle on the lower end thereof through the opening in the other of said first pair of members and into any portion of a body registering therewith.

2. A device as defined in claim 1, wherein said resilient means comprises a resilient strap secured at opposite ends to said one of said first pair of members adjacent diametrally opposite sides of the opening therein, said strap being insertable intermediate its end over a shoulder on said syringe releasably to support the syringe in its needle-down position in the last-named opening.

3. A device as defined in claim 2, wherein said strap comprises a rubber band having diametrally opposite sides thereof releasably engaged in notches formed in opposite ends of said one member of said first pair.

4. A device as defined in claim 1, wherein
a shoulder on the syringe is engageable with said one of said first pair of members around marginal portions of its opening, when the other of said additional members is moved to its fired position, thereby to limit the downward movement of the syringe in said openings, and the outside surfaces of said first pair of members are spaced from each other a distance slightly greater than the distance between the shoulder and needle of the syringe so that the needle will project a predetermined distance beyond said other of said first pair of members, when moved to its fired position.

5. A device as defined in claim 4, including a pair of spaced, parallel sidewalls interposed between said first pair of members to support the latter in spaced relation, said two additional members extending transversely between said side walls, and being spaced from the other of said first pair of members, whereby the lower end of said syringe remains visible when in its fired position.

6. A device for inserting the needle of a syringe into a body, comprising a base having a plane, lower surface disposed to be positioned against the surface of a body into which a syringe needle is to be inserted, and having therein a central opening, means mounted on the upper surface of said base for releasably supporting a syringe in a cocked position on said base, and with the needle thereof disposed in spaced, coaxial relation with said opening, said means including a movable latching member releasably engageable with said syringe adjacent its lower end releasably to prevent movement of the syringe toward said opening and resilient means releasably engageable with said syringe adjacent its upper end resiliently to urge said syringe against said latching member, when the latter is in a first position, and to urge said syringe downwardly to a second position in which the needle thereon projects through said opening and a predetermined distance beyond the lower surface of said base, when said latching member is moved to a second position, said base being made of transparent material, and said means for supporting said syringe further comprising a pair of spaced side members supporting said latching member above said base and forming between said base and said latching member an open space which permits the lower end of said syringe to be viewed when the syringe has been moved to its lowered position.

* * * * *